United States Patent [19]

Bürstinghaus et al.

[11] Patent Number: 4,568,668
[45] Date of Patent: Feb. 4, 1986

[54] OXIMINOPHOSPHORIC ACID DERIVATIVES, THEIR PREPARATION AND THEIR USE FOR CONTROLLING PESTS

[75] Inventors: Rainer Bürstinghaus, Weinheim; Walter Himmele, Walldorf; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 572,914

[22] Filed: Jan. 23, 1984

[30] Foreign Application Priority Data

Jan. 29, 1983 [DE] Fed. Rep. of Germany ....... 3302969

[51] Int. Cl.$^4$ .................. A01N 57/16; C07D 306/09; C07D 307/06
[52] U.S. Cl. ..................................... 514/99; 549/426; 549/218
[58] Field of Search ........................ 549/218; 424/203; 514/99

[56] References Cited

U.S. PATENT DOCUMENTS

| | | | |
|---|---|---|---|
| 2,957,016 | 10/1980 | Diamond | 260/461 |
| 3,591,662 | 7/1971 | Lorenz et al. | 260/940 |
| 3,639,537 | 2/1972 | Kaufman | 549/218 |
| 3,884,996 | 5/1975 | Lorenz et al. | 260/940 |
| 3,943,249 | 3/1976 | Stein et al. | 424/202 |
| 4,320,122 | 3/1982 | Theobald et al. | 424/200 |
| 4,327,090 | 4/1982 | Buerstinghaus et al. | 424/203 |

OTHER PUBLICATIONS

Stein et al., C.A., 79, 66160q (1973).

*Primary Examiner*—Nicky Chan
*Attorney, Agent, or Firm*—Keil & Weinkauf

[57] ABSTRACT

Oximinophosphoric acid derivatives of the formula I

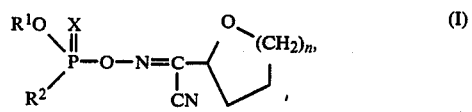

where $R^1$ is a straight-chain or branched alkyl group of not more than 4 carbon atoms, $R^2$ is a straight-chain or branched alkoxy or alkylthio group of not more than 4 carbon atoms, a straight-chain or branched alkyl group of not more than 3 carbon atoms, phenyl, amino, or a straight-chain or branched alkylamino or dialkylamino radical where each alkyl is of no more than 4 carbon atoms, X is oxygen or sulfur and n is 1 or 2, a process for their preparation, and their use for controlling pests.

3 Claims, No Drawings

OXIMINOPHOSPHORIC ACID DERIVATIVES, THEIR PREPARATION AND THEIR USE FOR CONTROLLING PESTS

The present invention relates to oximinophosphoric acid derivatives, a process for their preparation, pesticides which contain these derivatives as active ingredients, and a process for controlling pests using these active ingredients.

Oximinophosphoric acid derivatives are disclosed in German Published Application DAS No. 1,052,981 and DAS No. 1,238,902, and German Laid-Open Application DOS No. 2,304,848 and DOS No. 2,952,738, and are useful for controlling insects and arachnids. However, their action is not always completely satisfactory, particularly where a low concentration is used.

We have found that oximinophosphoric acid derivatives of the formula I

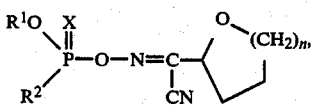

where $R^1$ is a straight-chain or branched alkyl group of not more than 4 carbon atoms, $R^2$ is a straight-chain or branched alkoxy or alkylthio group of not more than 4 carbon atoms, a straight-chain or branched alkyl group of not more than 3 carbon atoms, phenyl, amino, or a straight-chain or branched alkylamino or dialkylamino radical where each alkyl is of no more than 4 carbon atoms, X is oxygen or sulfur and n is 1 or 2, have a very good insecticidal, acaricidal and nematicidal action, and are superior to conventional active ingredients which have a similar structure of the same direction of action.

The oximinophosphoric acid derivatives of the formula I can be obtained by reacting an appropriate α-oximinonitrile with an appropriate (thiono)(thiol)phosphoric(phosphonic)acid ester(amide)halide:

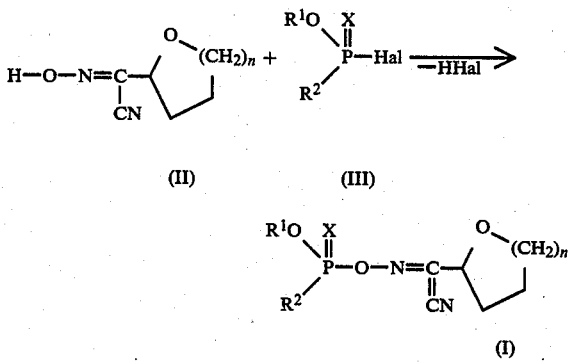

For economic reasons, halogen (Hal) is preferably chlorine.

The reaction is advantageously carried out in a solvent or diluent, suitable examples being aliphatic and aromatic hydrocarbons and chlorohydrocarbons, such as petroleum ether, benzene, toluene, xylene, gasoline, dichloromethane, chloroform, tetrachloromethane, 1,2-dichloroethane and chlorobenzene, ethers, such as diethyl ether, di-n-butyl ether, methyl tert.-butyl ether, tetrahydrofuran and dioxane, ketones, eg. acetone, methyl ethyl ketone and methyl isopropyl ketone, and nitriles, such as acetonitrile and propionitrile, as well as mixtures of these.

The basic agents conventionally used in the phosphorylation of hydroxy compounds are suitable acid acceptors. Alkali metal carbonates or alcoholates, eg. sodium carbonate, potassium carbonate, sodium methylate, potassium methylate, sodium ethylate and potassium ethylate, and aliphatic, aromatic and heterocyclic amines, eg. triethylamine, dimethylamine, piperidine, dimethylaniline, dimethylbenzylamine and pyridine, are particularly suitable. In some cases, it is advantageous to use an alkyl-lithium compound, eg. n-butyl-lithium, or an alkali metal hydride, eg. sodium hydride.

Instead of adding an acid acceptor, it is also possible to prepare a salt of the α-oximinonitrile (II), eg. an alkali metal, alkaline earth metal or ammonium salt, before the reaction, and to employ this salt in the reaction.

The starting materials are usually employed in stoichiometric amounts, but it is quite possible that an excess of one or other of these materials may be advantageous in specific cases.

The reaction usually takes place at an adequate velocity at above room temperature, and a temperature of 120° C. must in general not be exceeded. Since in some cases the reaction is accompanied by the production of heat, it may be advantageous to provide a means of cooling.

The reaction mixture is worked up in a conventional manner, for example by the addition of water, separation of the phases and distillation and/or column chromatography.

The α-oximinonitriles of the formula II which are used as starting materials for the preparation of the compounds I are novel. They can be prepared in a conventional manner (cf. German Published Application DAS No. 1,567,142) by chlorinating the corresponding 2-formyltetrahydropyran or -furan oxime of the formula IV and reacting the product with sodium cyanide or potassium cyanide in accordance with the following equation:

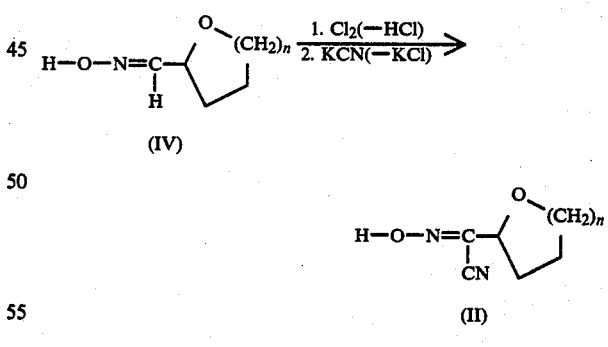

Oximes of the formula IV are obtained by reacting the appropriate 2-formyltetrahydropyran or -furan of the formula V with hydroxylamine hydrochloride in accordance with the following equation:

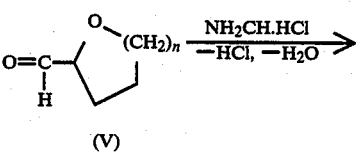

-continued

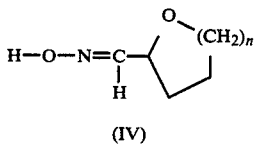

(IV)

The aldehydes V are known from the literature (cf. Bull. Chem. Soc. Jap. 45 (1972), 916–921; J. Amer. Chem. Soc. 95 (1973), 3635–3645; and Kogyo Kagaku Zasshi 71 (1968), 137–142 (C.A. 69, 86 757 m)).

The (thiono)(thiol)phosphoric(phosphonic)acid ester(amide)halides III furthermore required for the synthesis of the compounds of the formula I are disclosed in Houben-Weyl, Methoden der organischen Chemie, Volume XII/2, page 274 et seq., Georg Thieme Verlag, Stuttgart, 1964, and can be prepared by the synthesis routes described therein.

Some of the novel compounds of the formula I are obtained in the form of colorless or slightly brownish oils which can be freed from the final volatile constituents by prolonged heating at moderately elevated temperatures under reduced pressure (incipient distillation), and can be purified in this manner. If the compounds of the formula I are obtained in crystalline form, they can be purified by recrystallization.

Since the oximinophosphoric acid derivatives of the formula I can occur in the structurally isomeric syn and anti forms, their melting range or boiling range is of little use in characterizing them; hence, they have been characterized below on the basis of H-NMR spectra, elemental analysis and IR spectra with typical absorption maxima in the fingerprint region between 1,500 and 900 cm$^{-1}$.

The Examples which follow illustrate the preparation of the oximinophosphoric acid derivatives of the formula I.

Precursors

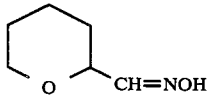

41.8 g of powdered sodium hydroxide were dissolved in a mixture of 100 ml of water and 315 ml of ethanol. 72.6 g of hydroxylamine hydrochloride in 70 ml of water were added to the cooled mixture, the precipitated sodium chloride was filtered off under suction, and the filtrate was added dropwise to 108.2 g of 2-formyltetrahydropyran at not more than 30° C., while stirring. The reaction mixture was stirred for a further 12 hours at room temperature, and was then poured into water. The aqueous phase was saturated with sodium chloride, and extracted with six times 100 ml of ether, the combined extracts were dried over sodium sulfate, and the solvent was stripped off, in the final stage under 0.05 mbar and at 35° C., to give 95.4 g of 2-formyltetrahydropyran oxime as a virtually colorless oil.

Yield: 78% of theory.

$C_6H_{11}NO_2$ (129)

calculated: C 55.8 H 8.6 N 10.8; found: C 55.9 H 8.7 N 11.0.

Infrared absorptions (cm$^{-1}$): 1,202, 1,085, 1,042, 970, 952, 940

2-Formyltetrahydrofuran oxime was prepared in a similar manner, the yield being similar.

$C_5H_9NO_2$ (115)

calculated: C 52.2 H 7.9 N 12.2; found: C 52.4 H 8.0 N 12.5.

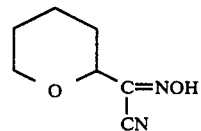

7.8 g of chlorine were passed into a cooled solution of 12.9 g of 2-formyltetrahydropyran oxime in 140 ml of ether at below 0° C. Thereafter, the volatile constituents of the reaction mixture were stripped off, the residue was taken up in 200 ml of methylene chloride, and the mixture was kept at room temperature for 24 hours. This liquid was then added dropwise to a suspension, cooled to 10°–15° C., of 6.8 g of potassium cyanide in 75 ml of methanol, and the mixture was stirred for a further 3 hours at room temperature. The precipitated potassium chloride was filtered off under suction, the filtrate was evaporated down, the residue was taken up in ether, the solution was washed three times with water and dried over magnesium sulfate, and the solvent was stripped off under 0.005 mbar and at 30° C. to give 11.3 g of α-oximino(tetrahydropyran-2-yl)-acetonitrile as a yellowish solid which melted from 45° C.

Yield: 74% of theory.

$C_7H_{10}N_2O_2$ (154)

calculated: C 54.6 H 6.6; found: C 54.8 H 6.8.

80 MHz H-NMR spectrum in CDCl$_3$ (δ values in ppm): 140–2.20 (m, 6H); 3.4–4.0 (m, 2H); 4.0–4.4 (m, 1H) 9.8–10.2 (broad, 1H).

α-Oximino-(tetrahydrofuran-2-yl)-acetonitrile was prepared in a similar manner, the yield being similar.

$C_6H_8N_2O_2$ (140)

calculated: C 51.4 H 5.8; found: C 51.1 H 6.2.

EXAMPLE 1

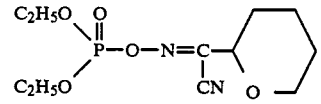

7.7 g of α-oximino-(tetrahydropyran-2-yl)-acetonitrile and 8.6 g of O,O-diethylphosphoryl chloride in 50 ml of acetonitrile were initially taken, and 3.8 g of powdered potassium carbonate were added a little at a time, while stirring. The reaction mixture was stirred for 24 hours at room temperature, after which insoluble material was filtered off under suction, the filtrate was evaporated down under reduced pressure, the residue was taken up in either, and the solution was washed three times with water, dried over sodium sulfate and freed from the solvent. Incipient distillation under 0.01 mbar and at 45° C. gave 12.8 g of (O,O-diethylphosphoryl)-α-oximino(tetrahydropyran-2-yl)-acetonitrile as a virtually colorless, viscous oil. Yield: 88.5% of theory.

$C_{11}H_{19}N_2O_5P$ (290)

calculated: C 45.5 H 6.6; found: C 45.3 H 6.6.

60 MHz H-NMR spectrum in CDCl$_3$ (δ values in ppm): 1.35 (t, 6H); 1.5–2.2 (m, 6H); 3.4–3.9 (m, 2H); 3.9–4.6 (m, 5H).

EXAMPLE 2

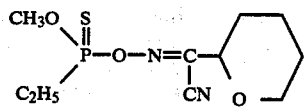

Using a procedure similar to that described in Example 1, reaction of 7.7 g of α-oximino-(tetrahydropyran-2-yl)-acetonitrile with 7.9 g of O-methyl-ethanethiophosphonyl chloride in the presence of 3.8 g of potassium carbonate gave 12.2 g (89% of theory) of (O-methyl-ethanethiophosphonyl)-α-oximino-(tetrahydropyran-2-yl)-acetonitrile as a yellowish oil.

$C_{10}H_{17}N_2O_3PS$ (276)

calculated: C 43.5 H 6.2; found: C 43.6 H 6.4.

Infrared absorptions ($cm^{-1}$): 1,086, 1,047, 1,025, 905.

EXAMPLE 3

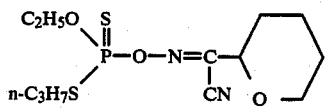

Using a procedure similar to that described in Example 1, 7.7 g of α-oximino-(tetrahydropyran-2-yl)acetonitrile were reacted with 10.9 g of O-ethyl-S-n-propyl-dithiophosphoryl chloride and 3.8 g of potassium carbonate to give 14.0 g (84% of theory) of (O-ethyl-S-n-propyl-dithiophosphoryl)-α-oximino-(tetrahydropyran-2-yl)-acetonitrile as a yellow oil.

$C_{12}H_{21}N_2O_3PS_2$ (332)

calculated: C 42.8 H 6.3 N 8.3; found: C 42.6 H 6.4 N 8.0.

Infrared absorptions ($cm^{-1}$): 1,088, 1,047, 1,020, 940, 906

The compounds listed in Table 1 below were likewise obtained by the route described in Example 1; other compounds of the formula (I) can be obtained in the same manner with appropriate modification of the methods according to the particular amount required, and if necessary, in order to obtain the best reaction conditions, after a preliminary experiment.

A few typical compounds I are shown in Table 2, these compounds having a biological action similar to that of the compounds shown in Table 1.

TABLE 1

| Example No. | $R^1$ | $R^2$ | X | n | $^1$H—NMR data (MHz, solvent, δ values) or IR absorptions ($cm^{-1}$). |
|---|---|---|---|---|---|
| 4 | $CH_3$ | $CH_3O$ | S | 2 | (60, $CDCl_3$) 1.4–2.2 (m, 6H); 3.2–3.8 (m, 2H); 3.9 (d, 6H); 3.9–4.5 (m; 1H) |
| 5 | $C_2H_5$ | $C_2H_5O$ | S | 2 | 1,086, 1,045, 1,020, 940, 903 |
| 6 | $C_2H_5$ | $C_2H_5$ | S | 2 | 1,086, 1,047, 1,020, 1,010, 940, 904 |
| 7 | $C_2H_5$ | NH—i.-$C_3H_7$ | O | 2 | (80, $CDCl_3$) 1.2 (d, 6H); 1.35 t, 3H); 1.5–2.2 (m, 6H); 3.0–3.8 (m, 3H); 3.8–4.5 (m, 4H) |
| 8 | $CH_3$ | $CH_3O$ | O | 2 | (80, $CDCl_3$) 1.6–2.2 (m, 6H); 3.4–3.9 (m, 2H); 3.9 (d, 6H); 3.9–4.5 (m, 1H) |
| 9 | $C_2H_5$ | S—n-$C_3H_7$ | O | 2 | (60, $CDCl_3$) 1.0 (t, 3H); 1.4 (t, 3H); 1.4–2.2 (m, 8H); 2.4–3.2 (2t; 2H); 3.3–3.75 (m, 2H); 3.8–4.6 (m, 5H) |

TABLE 2

| Example No. | $R^1$ | $R^2$ | X | n |
|---|---|---|---|---|
| 10 | $C_2H_5$ | $C_6H_5$ | S | 2 |
| 11 | $C_2H_5$ | S—sec.$C_4H_9$ | S | 2 |
| 12 | $C_2H_5$ | $(CH_3)_2N$ | O | 2 |
| 13 | $C_2H_5$ | $CH_3$ | S | 2 |
| 14 | $CH_3$ | $CH_3O$ | O | 1 |
| 15 | $CH_3$ | $CH_3O$ | S | 1 |
| 16 | $C_2H_5$ | $C_2H_5O$ | S | 1 |
| 17 | $C_2H_5O$ | $C_2H_5$ | O | 1 |
| 18 | $C_2H_5$ | $CH_3$ | S | 1 |
| 19 | $C_2H_5$ | $C_2H_5$ | S | 1 |
| 20 | $C_2H_5$ | C—n-$C_3H_7$ | S | 1 |
| 21 | $C_2H_5$ | NH—i-$C_3H_7$ | O | 1 |

The active ingredients listed above, and other active ingredients according to the invention, are used in the conventional manner for phosphates. Information concerning formulation, action and suitable mixing components for achieving synergistic and other advantageous actions can be found in, for example, U.S. Pat. No. 4,320,122, which is herein incorporated by reference.

The compounds I and II, whose formulae are given below and which are disclosed in German Laid-Open Application DOS No. 2,952,738, were selected and comparative substances.

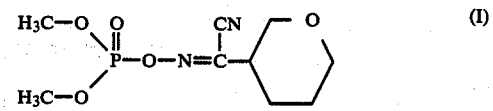

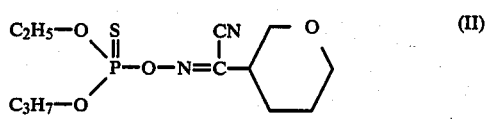

Use Example 1

Contact action on cockroaches (*Blatta orientalis*)

The bottom of 1 liter preserving jars was treated with a solution of the active ingredient in acetone. After the solvent had evaporated, 5 adult cockroaches were placed in each jar, and the mortality rate was determined after 48 hours.

In this experiment, the action of the active ingredients from Preparation Examples 1, 2, 4, 5 and 8 was up to 25 times more powerful than that of the two comparative substances.

Use Example 2

Long-term contact action on houseflies (*Musca domestica*)

The insides of Petri dishes having a diameter of 10 cm were treated with a solution of the active ingredient in acetone. After the solvent had evaporated, 20 4-day old houseflies were placed in the dishes. The mortality rate was determined after 4 hours.

In this experiment, the action of the active ingredients from Preparation Examples 1, 2, 4, 5 and 6 was up to 100 times more powerful than that of comparative substance I (which had the weaker action), and up to 10 times more powerful than that of compound II (which had the more powerful action).

Use Example 3

Contact action on granary weevil

Roughened glass plates measuring 8×8 cm were treated with a solution of the active ingredients in acetone. After the solvent had evaporated, 100 granary weevils were placed on the plates, and were covered with a watch glass having a diameter of 6 cm. After 4 hours, the weevils were transferred to untreated containers. The mortality rate was determined after 24 hours by ascertaining the number of weevils which, after this time, were able to emerge from an untreated cardboard dish (diameter 40 mm, height 10 mm) in the course of 60 minutes.

In this experiment, the action of the active ingredients from Preparation Examples 1, 2, 4, 5, 6 and 8 was not less powerful than that of the more effective comparative substance I, but was from 200 to 1,000 times more powerful than that of comparative substance II, which had a relatively weak action.

Use Example 4

Contact action on cotton stainers (*Dysdercus intermedius*)

Petri dishes having a diameter of 10 cm were lined with 1 ml of a solution of the active ingredient in acetone. After the solvent had evaporated, 20 larvae in the penultimate stage were introduced into each of the dishes, and the effect after 24 hours was recorded.

In this experiment, active ingredients 1, 2, 5 and 6 proved to be from 2 to 20 times more effective than comparative substances I and II.

Use Example 5

Diamondback moth caterpillars (*Plutella maculipennis*): stomach action and contact action Leaves of young cabbage plants were dipped for 3 seconds into an aqueous emulsion of the active ingredient, excess emulsion was allowed to drip off for a short time, and each leaf was then placed on a moistened filter paper in a Petri dish. 10 caterpillars in the 4th stage were then placed on the leaf, and the action was assessed after 48 hours.

In this experiment, active ingredients 1, 2, 4, 5, 6 and 7 achieved an about 80% action in concentrations down to one-tenth of that of the comparative substances.

Use Example 6

Contact action on ticks (*Ornithodorus moubata*)

The test was carried out on young ticks which had sucked blood only once. Groups of 5 animals in a commercially available tea-bag were dipped into the aqueous preparation of active ingredient for 5 seconds, after which the bag was suspended freely. After 48 hours, the mortality rate was determined.

Active ingredients 1, 5 and 8 proved completely effective in dilutions of 1 ppm, whereas the comparative substances had to be present in a concentration from 4 to 400 times higher in order to achieve a similar effect.

We claim:

1. An oximinophosphoric acid derivative of the formula I $$\begin{array}{c} R^1O \\ \phantom{R^1O}\diagdown \phantom{X} \underset{\phantom{X}}{\overset{X}{\|}} \\ \phantom{R^1O\diagdown}P-O-N=C- \\ R^2 \phantom{\diagup} \phantom{P-O-N=}| \\ \phantom{R^2\diagup P-O-N=}CN \end{array} \begin{array}{c} O \\ \diagdown \\ \phantom{O}(CH_2)_{n'} \\ \diagup \end{array} \quad (I)$$

where $R^1$ is a straight-chain or branched alkyl group of not more than 4 carbon atoms, $R^2$ is a straight-chain or branched alkoxy or alkylthio group of not more than 4 carbon atoms, a straight-chain or branched alkyl group of not more than 3 carbon atoms, phenyl, amino, or a straight-chain or branched alkylamino or dialkylamino radical where each alkyl is of no more than 4 carbon atoms, X is oxygen or sulfur and n is 1 or 2.

2. A pesticide which contains a solid or liquid carrier and an effective amount of one or more oximinophosphoric acid derivatives of the formula I as claimed in claim 1.

3. A method of controlling pests, wherein an effective amount of an oximinophosphoric acid derivative as claimed in claim 1 is allowed to act on pests or on their habitat.

* * * * *